US009714925B2

(12) United States Patent
Akmal et al.

(10) Patent No.: US 9,714,925 B2
(45) Date of Patent: Jul. 25, 2017

(54) SIMULATANEOUS GAS CHROMATOGRAPH ANALYSIS OF A MULTI-STREAM NATURAL GAS UPGRADE GENERATED THROUGH A MULTI-MEMBRANE PROCESS

(71) Applicant: Saudi Arabian Oil Company, Dhahran (SA)

(72) Inventors: Naim Akmal, Dhahran (SA); Saeed Hasan Al-Shahrani, Dammam (SA); Anwar H. Al-Khawajah, Dammam (SA); Milind M. Vaidya, Auburndale, MA (US); Jean-Pierre R. Ballaguet, Thenisy (FR); Sebastien A. Duval, Neuilly sur Seine (FR)

(73) Assignee: Saudi Arabian Oil Company, Dhahran (SA)

( * ) Notice: Subject to any disclaimer, the term of this patent is extended or adjusted under 35 U.S.C. 154(b) by 351 days.

(21) Appl. No.: 14/548,432

(22) Filed: Nov. 20, 2014

(65) Prior Publication Data

US 2016/0146764 A1    May 26, 2016

(51) Int. Cl.
*G01N 30/04* (2006.01)
*B01D 53/00* (2006.01)
(Continued)

(52) U.S. Cl.
CPC ........... *G01N 30/04* (2013.01); *B01D 53/002* (2013.01); *B01D 53/225* (2013.01); *B01D 53/30* (2013.01);
(Continued)

(58) Field of Classification Search
CPC ...... G01N 30/04; G01N 30/46; G01N 30/025; G01N 30/8854; B01D 53/002;
(Continued)

(56) References Cited

U.S. PATENT DOCUMENTS 5,199,962 A * 4/1993 Wijmans ................ B01D 53/22
95/39
5,709,732 A * 1/1998 Prasad ................ B01D 53/226
95/45

(Continued)

FOREIGN PATENT DOCUMENTS

EP          2732865 A2    5/2014
WO       03078999 A2    9/2003
(Continued)

OTHER PUBLICATIONS

Internet: http://www2.emersonprocess.com/siteadmincenter/PM%20Danalyzer%20Documents/DANGC_PDS_71-PDS-NGC-Model700.pdf Accessed Nov. 14, 2014.
(Continued)

*Primary Examiner* — Natalie Huls
*Assistant Examiner* — Monica S Young
(74) *Attorney, Agent, or Firm* — Dinsmore & Shohl LLP

(57) ABSTRACT

A gas chromatographic method for analyzing natural gas and a natural gas upgrading system using the gas chromatographic method for analyzing natural gas. The method includes transporting the natural gas through a chiller, transporting the natural gas from the chiller to at least two gas upgrading membranes, and operating a gas chromatographic system having at least one upstream gas chromatograph and at least two downstream gas chromatographs. The at least one upstream gas chromatograph, the first downstream gas chromatograph, and the second downstream gas chromatograph all operate simultaneously and utilize the same heating oven to heat samples of natural gas.

17 Claims, 2 Drawing Sheets

(51) Int. Cl.
  B01D 53/22 (2006.01)
  B01D 53/30 (2006.01)
  C10L 3/10 (2006.01)
  C10G 5/06 (2006.01)
  *G01N 30/02* (2006.01)
  *G01N 30/46* (2006.01)
  *G01N 30/88* (2006.01)

(52) U.S. Cl.
  CPC ............. *C10G 5/06* (2013.01); *C10L 3/10* (2013.01); *B01D 2257/102* (2013.01); *B01D 2257/304* (2013.01); *B01D 2257/504* (2013.01); *B01D 2257/702* (2013.01); *B01D 2257/80* (2013.01); *G01N 30/46* (2013.01); *G01N 2030/025* (2013.01); *G01N 2030/8854* (2013.01); *Y02C 10/10* (2013.01)

(58) Field of Classification Search
  CPC  B01D 53/30; B01D 53/225; B01D 2257/102; B01D 2257/504; B01D 2257/702; B01D 225/80; C10G 21/00; C10G 21/06; C10G 21/10; Y02C 10/10
  USPC ....................................................... 73/23.41
  See application file for complete search history.

(56) References Cited

U.S. PATENT DOCUMENTS

| | | | |
|---|---|---|---|
| 6,035,641 A | 3/2000 | Lokhandwala et al. | |
| 6,112,602 A | 9/2000 | Mitra et al. | |
| 6,153,097 A * | 11/2000 | Jensvold | B01D 63/026 210/321.79 |
| 6,374,860 B2 | 4/2002 | Xu et al. | |
| 6,701,774 B2 | 3/2004 | Srinivasan et al. | |
| 6,838,288 B2 | 1/2005 | Beens | |
| 7,281,408 B2 | 10/2007 | Srinivasan et al. | |
| 7,490,506 B2 | 2/2009 | Chaintreau et al. | |
| 2002/0007858 A1* | 1/2002 | Xu | F16K 27/003 137/828 |
| 2006/0198780 A1* | 9/2006 | Ota | B01D 53/62 423/418.2 |
| 2006/0243133 A1* | 11/2006 | Hart | B01D 53/047 95/26 |
| 2007/0204749 A1* | 9/2007 | Adkins | G01N 30/6034 96/101 |
| 2009/0150087 A1 | 6/2009 | Steinecker | |
| 2010/0154511 A1 | 6/2010 | Lambertus et al. | |
| 2010/0186586 A1 | 7/2010 | Chinn et al. | |
| 2010/0223950 A1* | 9/2010 | Malsam | C10L 3/10 62/611 |
| 2012/0157743 A1 | 6/2012 | Liu et al. | |

FOREIGN PATENT DOCUMENTS

| | | |
|---|---|---|
| WO | 2011036279 A1 | 3/2011 |
| WO | 2011147974 A1 | 12/2011 |

OTHER PUBLICATIONS

Internet: http://www2.shimadzu.com/applications/GC/NewGenCapillaryAFT.pdf Accessed Nov. 14, 2014.
Internet: http://www.yokogawa.com/an/download/bulletin/Bulletin11B08A01-01E.pdf Accessed Nov. 14, 2014.
International Search Report and Written Opinion dated Feb. 9, 2016 pertaining to International Application No. PCT/US2015/057327.

* cited by examiner

SIMULATANEOUS GAS CHROMATOGRAPH ANALYSIS OF A MULTI-STREAM NATURAL GAS UPGRADE GENERATED THROUGH A MULTI-MEMBRANE PROCESS

BACKGROUND

Field

Embodiments of the present disclosure generally relate to processing of natural gas and, more specifically relate to real-time monitoring of natural gas composition during a natural gas upgrading operation.

Technical Background

The demand for natural gas is continually increasing at least in part because of its usefulness to produce energy as well as its applicability to additional applications in the petrochemicals industry. Many new fields of natural gas recently discovered in locations such as Saudi Arabia contain high levels of acid gases (hydrogen sulfide and carbon dioxide) and nitrogen. The high content of acid gases and nitrogen in natural gas limits its use as a source of energy due to low BTU values as the quality and market value of produced natural gas depends on its composition. The presence of high content of nitrogen, hydrogen sulfide and/or carbon dioxide is one of the main reasons for the non-applicability of a natural gas in producing energy and/or applications in the petrochemicals industry. The abundance of non-useful natural gas produces new opportunities to make the non-useful natural gas useful by selectively removing components such as nitrogen, moisture and acid gases. Selective removal of these components has been achieved by cryogenic technique, use of membranes, or pressure swing adsorption (PSA) techniques. In some cases a combination of two or three techniques has been applied to achieve desired results. The selective removal process of undesired components from the bulk gas is assisted by reliable and continuous monitoring of the process. Such monitoring can be accomplished by using techniques such as gas chromatograph or other spectroscopic or laser based techniques. During the development of a new or improved process, it is essential to know the performance of the upgrading module by precisely determining the composition of incoming and outgoing gaseous products on a continuous basis.

Traditional gas chromatograph techniques have the accuracy limitation of more than ±3%, when used in series; meaning if two different gas chromatographs are used on a single application, at least a ±3% variation is anticipated between the results for the same gas sample. The goal of upgrading of natural gas involves use of cryogenic, membrane based or similar techniques, in which case, the processing results are dependent on the temperature, pressure, flow, and presence of moisture in the gas stream. Any change in the process upgrading configuration can result in a 1 to 2 percent improvement in the composition of the processed gas. Monitoring of such minute change in the composition of the processed gas is important in making a selection of the most appropriate membrane or modifying an existing membrane or similar upgrading technique.

Gas chromatographs and other analyzer techniques have been in use since the early stages of gas upgrading processes, yet the conventional use of multiple gas chromatographs lack accuracy. Hence present systems are unable to differentiate minute changes in the composition of the natural gas while being processed. Accordingly, ongoing needs exist for an improved method of determining minute changes in the composition in real time of natural gas during processing is desired.

SUMMARY

Referring to FIG. 1, embodiments of the present disclosure are directed to a process of monitoring continuous upgrading of natural gas using an integrated gas chromatographic system. The methods and systems of the present disclosure have industrial applicability, specifically in the oil, gas, and power industries due to the abundance of non-useful natural gas obtained from new natural gas fields. There are opportunities to make the non-useful natural gas from new natural gas fields useful by selectively removing components such as nitrogen, moisture and acid gases.

According to one embodiment, a gas chromatographic method for analyzing natural gas is provided. The method includes transporting the natural gas through a chiller and from the chiller to at least two gas upgrading membranes. The two gas upgrading membranes include at least three upgraded product stream outlets placed to provide a first cut of upgraded natural gas, a second cut of upgraded natural gas, and a third cut of upgraded natural gas respectively. The method further includes operating a gas chromatographic system having at least one upstream gas chromatograph and at least two downstream gas chromatographs, the at least two downstream gas chromatographs including a first downstream gas chromatograph and a second downstream gas chromatograph. Additionally, the at least one upstream gas chromatograph, the first downstream gas chromatograph, and the second downstream gas chromatograph all operate simultaneously, the at least one upstream gas chromatograph, the first downstream gas chromatograph, and the second downstream gas chromatograph are all calibrated using the same calibration feed, and the at least one upstream gas chromatograph, the first downstream gas chromatograph, and the second downstream gas chromatograph all utilize the same heating oven to heat samples of natural gas. Further, the method includes transporting samples of natural gas to the gas chromatographic system. Specifically, a sample of the natural gas exiting the chiller, a sample of the natural gas entering a first membrane of the at least two gas upgrading membranes, and a sample of the natural gas entering a second membrane of the at least two gas upgrading membranes are transported to the at least one upstream gas chromatograph, and a sample of the upgraded natural gas exiting each of the upgraded product stream outlets are transported to the at least two downstream gas chromatographs. Finally, the method includes monitoring the composition of the sample of the natural gas exiting the chiller, the sample of the natural gas entering a first membrane of the at least two gas upgrading membranes, the sample of the natural gas entering a second membrane of the at least two gas upgrading membranes, and the samples of the upgraded natural gas exiting each of the product stream outlets with a controller to determine upgrading of the natural gas.

In an alternative gas chromatographic method embodiment, the method may include transporting a sample of the natural gas entering the chiller to the at least one upstream gas chromatograph in addition to, or in lieu of, transporting a sample of the natural gas exiting the chiller to the at least one upstream gas chromatograph.

In a further embodiment, a natural gas upgrading system having a gas chromatographic system, a chiller, at least two gas upgrading membranes, and a controller is provided. The gas chromatographic system includes at least one upstream gas chromatograph and at least two downstream gas chromatographs with the at least two downstream gas chromatographs representing a first downstream gas chromatograph and a second downstream gas chromatograph. Additionally, the chiller is fluidly connected to the at least two gas upgrading membranes and is configured to remove heavy hydrocarbons from a natural gas supply feed. Further, the at least two gas upgrading membranes are configured to selectively allow certain gases to permeate therethrough to remove impurities from the natural gas. Each gas upgrading membrane also includes an inlet and at least three product stream outlets placed to provide a first cut of upgraded natural gas, a second cut of upgraded natural gas, and a third cut of upgraded natural gas respectively. Additionally, the at least one upstream gas chromatograph is fluidly connected to the exit of the chiller, the inlet of a first membrane of the at least two gas upgrading membranes, and the inlet of a second membrane of the at least two gas upgrading membranes allowing for transport of samples to the at least one upstream gas chromatograph. Similarly, each of the product stream outlets is fluidly connected to at least one of the at least two downstream gas chromatographs for transport of samples to the at least two downstream gas chromatographs. Further, the controller is configured to monitor the composition of the samples of the natural gas from the exit of the chiller, the inlet of the first membrane of the at least two gas upgrading membranes, the inlet of the second membrane of the at least two gas upgrading membranes, and the samples from each of the product stream outlets to determine upgrading of the natural gas. Finally, the at least one upstream gas chromatograph and the at least two downstream gas chromatographs are configured to operate simultaneously, are calibrated by a single calibration gas feed, and a single heating oven or set of heating ovens in series is provided to heat natural gas samples for the at least one upstream gas chromatograph and the at least two downstream gas chromatographs.

Additional features and advantages of the embodiments described herein will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Figure 1:
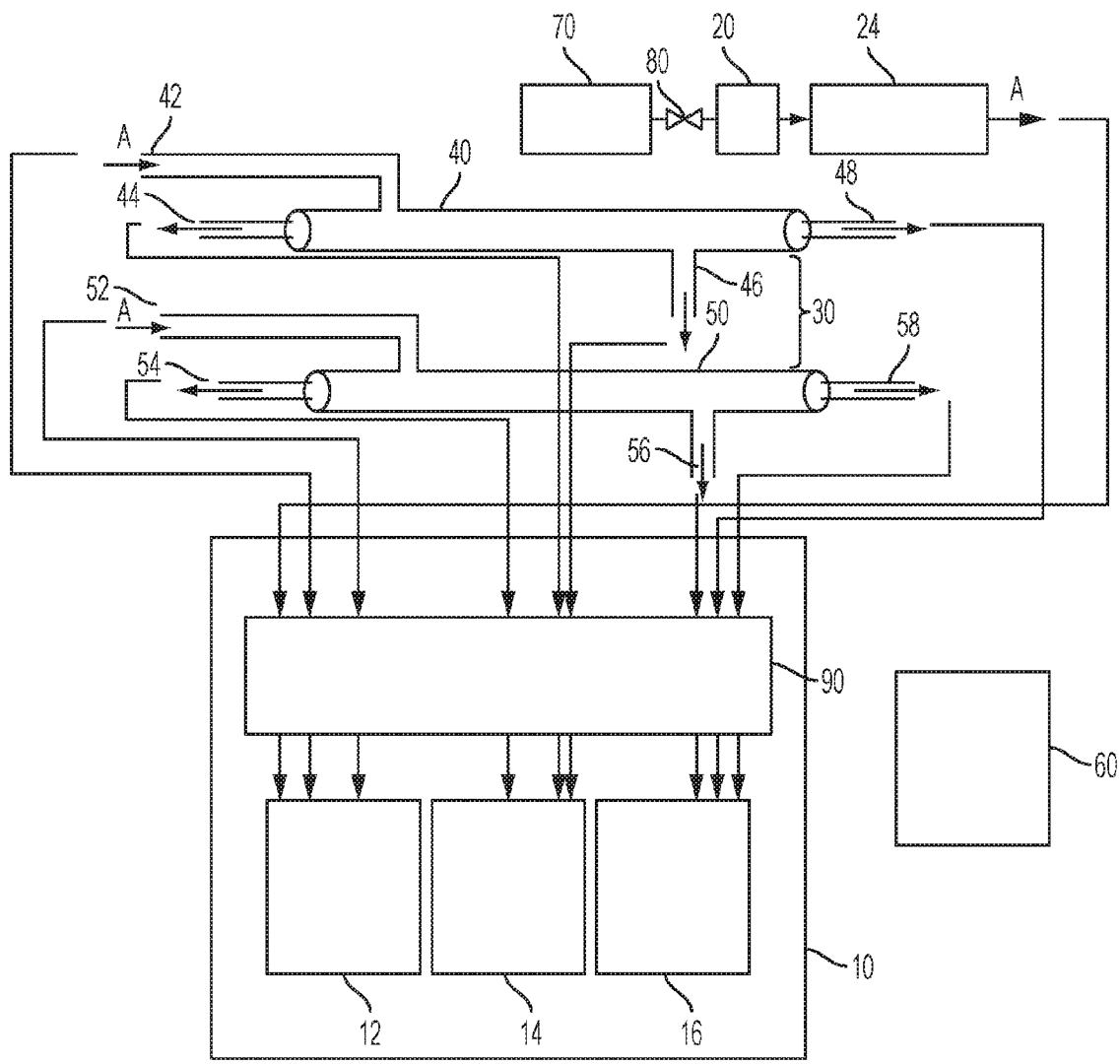
FIG. 1 is a schematic illustration of an integrated analyzer in accordance with one or more embodiments of the present disclosure.
Figure 2:
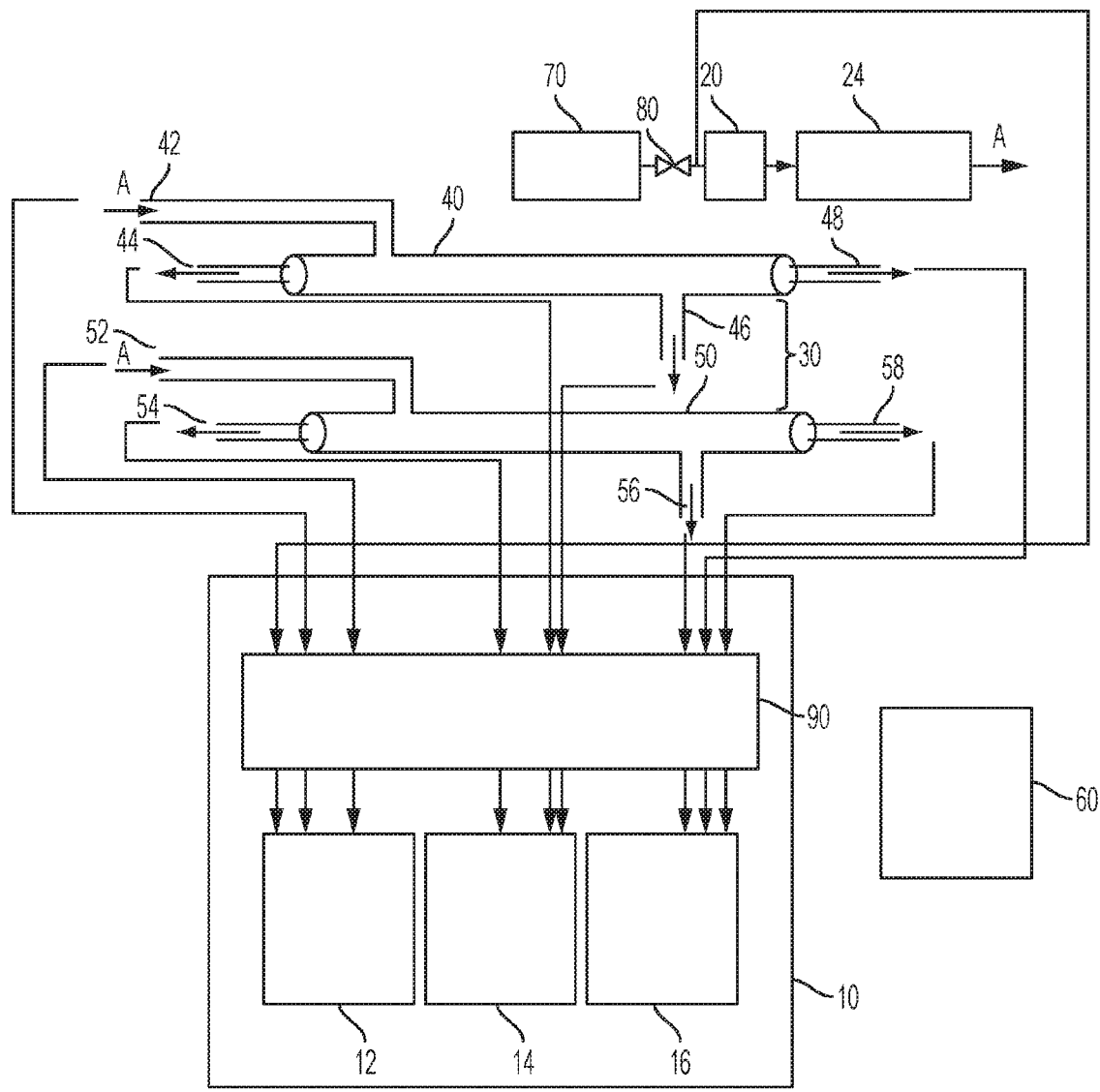
FIG. 2 is a schematic illustration of an integrated analyzer in accordance with one or more embodiments of the present disclosure.

Reference will now be made in detail to embodiments of the natural gas upgrading system and method of the present disclosure. Though the system of FIG. 1 is provided as exemplary, it should be understood that the present systems and methods encompass other configurations.

Generally, the invention relates to a process of monitoring continuous upgrading of natural gas using integrated gas chromatography in a mode that allows for the measurement of changes in the composition of gases at different stages of separation and upgrading. The analytical method is based on an integrated gas chromatographic system, which has multiple chromatographs utilizing a single heating oven. Use of such integrated multiple chromatographic system allows all the chromatographic separation entities to be exposed to the same environment. A consistent environment between individual chromatographs allows small changes in the process to be monitored and quantified.

The integrated gas chromatographic system works on the principles of basic gas chromatography using injectors, columns and detectors. The integrated gas chromatographic system is capable of quantifying various compositional components when properly calibrated using internal or external calibration technique. However, the analytical data received from typical stand-alone gas chromatographs have ±3% variation when the same sample stream is analyzed on two different gas chromatographs, even when calibrated using the same calibration gas. The reason for such variation is believed due to using two different heating ovens, different modes of delivery of samples, and independent controllers dedicated to each chromatograph. Conversely, the integrated gas chromatographic system described further herein is independent of many of these variables such as multiple independent heating ovens, different modes of delivery of samples, and independent controllers dedicated to each chromatograph. The reduction in variables between the analyses of each gas chromatograph as a result of the synergistic combination of a single heating oven, a single controller, and consistent sample delivery reduces the deviation between gas chromatographs to less than ±1%. As a reliable measurement for small changes in the composition of gases is necessary when evaluating natural gas upgrading performance, a ±3% variation in analytical result is too high as changes in composition are hidden in the variance, whereas the reduction to less than ±1% allows the evaluation to occur.

The separation of natural gas is performed to remove inerts or sour gas content components such as nitrogen, hydrogen sulfide, carbon dioxide and water from the total composition of the natural gas stream. The upgrading process increases the molar content of various hydrocarbons present in the gas stream, particularly the content of methane gas, which is more preferred in a natural gas when sold. As the separation of various components from natural gas depends on flow, temperature, pressure and water content of the gas, it is extremely important to know the change in the efficiency of the natural gas separation and upgrading process. A minor change in the physical properties of the provided natural gas, such as changed flow, temperature, pressure, or water content, can lead to differing performance of the separation and upgrading process, thereby causing changes in the composition of gases from the sample stream. Such changes can be measured, only if the analytical instrument attached to the process is sensitive enough to measure the differential composition between the incoming gas and the processed upgraded gas.

One general process for upgrading natural gas involves passage of the natural gas through upgrading membranes. Specifically, in order to perform the upgrading of the natural gas, the natural gas is initially passed through a series of steps in which heavy hydrocarbons and excess water is removed. Additionally, any particulates and carbon material is dropped out of the natural gas stream prior to upgrading and the associated analysis of the natural gas stream. Then a gas upgrading membrane, discussed in detail below, separates components of the natural gas stream to provide multiple upgraded natural gas streams with varying final compositions. Samples of the natural gas and each of the upgraded natural gas streams are then mixed with a carrier gas, such as helium, hydrogen, or nitrogen, and provided to a gas chromatograph. The samples are introduced into the columns of gas chromatographs capable of separating components present in the sample stream based on polarity, boiling point, and other criteria of separation. Each component after proper separation is passed through a series of detectors in the gas chromatograph and its presence is reported using dedicated software. The reporting of the components in the feed natural gas stream and each of the upgraded natural gas streams allows for changes to the operational parameters of the system as well as monitoring of the performance of the gas upgrading membranes.

Referring to the embodiment of FIG. 1, a natural gas upgrading system 100 is shown. The natural gas upgrading system 100 comprising a gas chromatographic system 10, a chiller 20, at least two gas upgrading membranes 30, and a controller 60. As shown in FIG. 1, the gas chromatographic system 10 comprises at least one upstream gas chromatograph 12 and at least two downstream gas chromatographs comprising a first downstream gas chromatograph 14 and a second downstream gas chromatograph 16.

The chiller 20 is a device which reduces the temperature of a stream passing through, for example, a natural gas supply feed 70. As a result the composition of the natural gas supply feed 70 changes as certain components precipitate and/or condense out. Non-limiting examples of chillers 20 include model C9600AS from Pioneer Air Systems Inc. Wartburg, Tenn. Chillers are additionally manufactured by, for example, TRANE, a unit of Ingersoll Rand.

The chiller 20 is configured to remove heavy hydrocarbons from a natural gas supply feed 70 and is fluidly connected to the at least two gas upgrading membranes 30. In various embodiments, the heavy hydrocarbons are defined as those being C5 or above, meaning the central carbon chain consists of at least 5 carbon atoms. In further embodiments, the heavy hydrocarbons are defined as those being C7 or above, meaning the central carbon chain consists of at least 7 carbon atoms. In yet further embodiments, the heavy hydrocarbons are defined as those being C9 or above, meaning the central carbon chain consists of at least 9 carbon atoms.

The chiller 20 reduces the temperature of the natural gas provided by the natural gas supply feed 70 passing therethrough. The reduction in temperature of the natural gas provided by the natural gas supply feed 70 results in condensation of various components of the natural gas. Specifically, the reduction in temperature assists in removal of the heavy hydrocarbons as they condense from a gaseous state to a liquid state as well as water as it condenses from a water vapor to liquid water. For example, the chiller 20 may operate as a recirculating water system. The vapor to be condensed is circulated through a condensing coil, which is continually wetted on the outside by a recirculating water system. Air is blown upward over the coil, causing a small amount of water to evaporate. This evaporation removes heat from the coil, cooling and condensing the vapor in the coil to temperatures lower than either air-cooled or water-cooled condensers. In embodiments, the temperature of the natural gas is dropped to approximately 85° F. using this technique. Under normal operating conditions of at least one embodiment the total natural gas flow is approximately 8 million SCF (standard cubic foot)/day through the chiller 20, however, one having skill in the art world appreciate that the chiller may be scaled for different desired natural gas flow. Additionally, the chiller 20 has design characteristics allowing operation in a Class I Division 2 Group D classified area.

The at least two gas upgrading membranes 30 are configured to selectively allow certain gases to permeate, thus removing impurities from the natural gas supply feed 70. In an embodiment, the at least two gas upgrading membranes 30 comprise a first membrane 40 and a second membrane 50. The first membrane 40 comprises a first membrane inlet 42 and at least three product stream outlets 44,46,48 placed to provide a first cut of upgraded natural gas, a second cut of upgraded natural gas, and a final cut of upgraded natural gas respectively. Similarly, the second membrane 50 comprises a second membrane inlet 52 and at least three product stream outlets 54,56,58 placed to provide a first cut of upgraded natural gas, a second cut of upgraded natural gas, and a third cut of upgraded natural gas respectively. For purposes of this disclosure a cut is defined as the certain composition of natural gas at a given temperature, pressure and flow rate passing through layers of the gas upgrading membranes 30 which yields product streams of differing compositions. One having skill in the art would appreciate the similarity to product streams from a distillation process of crude oil which produces, for example, a naphtha cut, a kerosene cut, a diesel oil cut, heavy fuel oil cuts, and bottoms product from the different fractions removed from the distillation process.

Upgraded natural gas comprises crude natural gas with excess and undesirable components such as nitrogen, moisture and acid gases reduced or removed. A preferred composition of upgraded natural gas is one that produces btu value of 1020-1050. As a basic rule, when the percentage of nitrogen goes above 10% the btu value falls dramatically leading to a low value gas. However, crude natural gas generally has high nitrogen content which is typically over approximately 13% and methane generally in the range of 65-70% (v/v). Additionally, crude natural gas may contain approximately 1-4% acid gases such as $H_2S$ and $CO_2$.

In embodiments, the at least one upstream gas chromatograph 12 is fluidly connected to the exit of the chiller 20, the first membrane inlet 42, and the second membrane inlet 52 for transport of samples to the at least one upstream gas chromatograph 12. Additionally, each of the product stream outlets 44,46,48,54,56,58 is fluidly connected to at least one of the at least two downstream gas chromatographs 14,16 for transport of samples to the first downstream gas chromatograph 14 and the second downstream gas chromatograph 16.

None-limiting examples of the at least one upstream gas chromatograph 12 and the at least two downstream gas chromatographs 14,16 include the ProGC+ (Thermo Fisher Scientific Inc), and gas chromatographs from Yokogawa, ABB, and Emerson.

The controller 60 is configured to monitor the composition of the samples of the natural gas from the exit of the chiller 20, the first membrane inlet 42, the second membrane inlet 52, and the samples from each of the product stream outlets 44,46,48,54,56,58 to determine upgrading of the natural gas supply feed 70. In various embodiments, the controller 60 is a programmable logic controller (PLC). In further embodiments, the controller 60 is a microprocessor. The controller 60 may be a stand-alone unit receiving data from each gas chromatograph or may be integrated into at least one of the gas chromatographs A dedicated sample handling system is provided to transport samples of natural gas for analyses. As previously indicated, numerous connections are provided between the gas chromatographic system 10 and sampling points such as the first membrane inlet 42, the product stream outlets 44,46,48,54,56,58, or the exit of the chiller 20. The total number of sampling points is limited only by the number of gas chromatographs in the gas chromatographic system 10 and the frequency at which sample analysis of each sampling point is desired. In various embodiments, at least 9 sampling points are provided. In further embodiments, at least 15 sampling points are provided. In yet further embodiments, at least 25 sampling points are provided.

As only a single sample may be analyzed on a given gas chromatograph at a time, the number of sampling points fluidly connected to each individual gas chromatograph in the gas chromatographic system 10 determines the frequency at which the natural gas composition at each sampling point may be determined. The analysis time for each stream can range from a few minutes to over an hour and thus if three sampling points are connected to a single gas chromatograph is may be as little as a few minutes or as much as multiple hours between sampling and analysis at a given sampling point. In various embodiments, one or multiple individual gas chromatographs in the gas chromatographic system 10 are each connected to a single sampling point providing a dedicated gas chromatograph. In further embodiments, each gas chromatograph in the gas chromatographic system 10 is connected to 3 sampling points. In yet further embodiments, each gas chromatograph in the gas chromatographic system 10 is connected to 5 sampling points. In still further embodiments, each sampling point is connected to multiple gas chromatographs in the gas chromatographic system 10, allowing the specific samples being simultaneously analyzed to vary.

Each sampling point has the potential to contain from two to twenty or more components, depending on the composition of the sample stream. These components are mostly hydrocarbons, nitrogen, and acid gases such as hydrogen sulfide and carbon dioxide.

In addition to hydrocarbons, acid gases, and nitrogen, the sample may also contain moisture. In various embodiments the controller 60 analyzes all components present in the sample stream except moisture content. In further embodiments, the controller 60 analyzes all components present in the sample stream plus any water present in gas phase at atmospheric or operating temperature.

The at least one upstream gas chromatograph 12 and the at least two downstream gas chromatographs 14,16 are configured to operate simultaneously. Specifically, each of the at least one upstream gas chromatograph 12 and the at least two downstream gas chromatographs 14,16 analyze a different sample concurrently. Simultaneous operation of each of the gas chromatographs in the gas chromatographic system 10 additionally allows for analysis of the effectiveness of a single one of the at least two gas upgrading membrane 30 without concern about the time required for the actual analysis. For example, the at least one upstream gas chromatograph 12 analyzes a sample from the first membrane inlet 42, the first downstream gas chromatograph 14 analyzes a sample from the product stream outlet providing a first cut of upgraded natural gas 44, and the second downstream gas chromatograph 16 analyzes a sample from the product stream outlet providing a final cut of upgraded natural gas 48 all simultaneously providing a real-time analysis of the effectiveness of the first membrane 40. Conversely, without simultaneous operation of the gas chromatographs in the gas chromatographic system 10 the collected compositional date from a sample from the first membrane inlet 42, a sample from the product stream outlet providing a first cut of upgraded natural gas 44, and a sample from the product stream outlet providing a final cut of upgraded natural gas 48 would not necessarily be temporally similar and thus not able to account for fluctuations in the sample from the first membrane inlet 42 when analyzing the effectiveness of the first membrane 40.

Additionally, the at least one upstream gas chromatograph 12 and the at least two downstream gas chromatographs 14,16 are calibrated by a single calibration gas feed. The contents of the single calibration gas feed are based on the number of components to be analyzed by the integrated gas chromatographic system. Specifically, the calibration gas is formulated to approximately match the composition of the natural gas stream to be analyzed. In specific embodiments, the base component of the calibration gas is nitrogen. Nitrogen in the calibration gas is beneficial as upgrading of natural gas is performed by reducing the amount of nitrogen present in the natural gas. In further embodiments, the calibration gas is prepared with another inert gas as the base component.

Cylinders or other commonly known vessels of certified calibration gas can be purchased from vendors specialized in providing certified calibration gas mixtures. In various embodiments, certified gas vessels, such as cylinders, are purchased from two different vendors. The calibration gas mixture received from one vendor is used to calibrate each of the gas chromatographs in the gas chromatographic system 10 and then the calibration gas from the second vendor is utilized to verify the accepted calibration of each of the gas chromatographs as a validation process. In further embodiments, the calibration gas mixture received from a single vendor is used to calibrate each of the gas chromatographs in the gas chromatographic system 10 with no separate validation.

A single calibration gas provides more precise measurements between individual gas chromatographs in the gas chromatographic system 10. Specifically, calibrating each gas chromatograph with a calibration gas consisting of the same composition provides identical calibrations for each gas chromatograph. When calibration gases with different compositions are utilized, slight variations in the calibrations of the sensors of the gas chromatographs can provide differing results. For example, a calibration gas with more a higher mole % of ethane or propane might provide a calibration slightly different than one higher in nitrogen or carbon dioxide. This is additionally why it is desirable for the calibration gas to approximately represent the actual composition of the natural gas.

A single heating oven 90 or set of heating ovens in series is provided to heat natural gas samples for the at least one upstream gas chromatograph 12 and the at least two downstream gas chromatographs 14,16. The column of a gas chromatograph may be contained in a heating oven, the temperature of which is precisely controlled. The rate at which a sample passes through the column is directly proportional to the temperature of the column. The higher the column temperature, the faster the sample moves through the column. However, the faster a sample moves through the column, the less it interacts with the stationary phase of the column, and the less the analytes are separated. Thus, a single heating oven 90 housing the columns for all the gas chromatographs of the gas chromatographic system 10 provides a consistent rate of passage of samples through the column regardless of the particular gas chromatograph used. The consistent rate of passage of samples through the column regardless of the particular gas chromatograph used is achieved because the columns of each of the various gas chromatographs are all heated to the same temperature by the same oven. Variability in thermostats or the heat generation capacity between multiple ovens is eliminated. The consistent rate of passage of samples though the column is desirable as that reduces variations between individual gas chromatographs allowing analyses from the at least one upstream gas chromatograph 12, the first downstream gas chromatograph 14, and the second downstream gas chromatograph 16 to be directly compared.

In various embodiments, the product stream outlet 44 placed to provide the first cut of upgraded natural gas of the first membrane 40 and the product stream outlet 54 placed to provide the first cut of upgraded natural gas of the second membrane 50 are fluidly connected to the first downstream gas chromatograph 14.

Further, in various embodiments, the product stream outlet 46 placed to provide the second cut of upgraded natural gas of the first membrane 40 is fluidly connected to the first downstream gas chromatograph 14 and the product stream outlet 56 placed to provide the second cut of upgraded natural gas of the second membrane 50 is fluidly connected to the second downstream gas chromatograph 16.

In yet further embodiments, the product stream outlet 48 placed to provide the third cut of upgraded natural gas of the first membrane 40 and the product stream outlet 58 placed to provide the third cut of upgraded natural gas of the second membrane 50 are fluidly connected to the second downstream gas chromatograph 16.

While detailed connections of specific sampling points to each of the at least one upstream gas chromatograph 12, the first downstream gas chromatograph 14, and the second downstream gas chromatograph 16 are provided in various embodiments, it is not necessary to connect the sampling points to the gas chromatographs in the specific arrangements provided. It is equally possible and envisioned to analyze samples from the sampling points using any available gas chromatograph in the gas chromatographic system 10.

In various embodiments, the controller 60 is coupled to a flow regulator 80 to controllably adjust the rate at which the natural gas supply feed 70 is provided to the chiller 20. Non-limiting examples of flow regulators include adjustable valves and pumps. The flow rate through the chiller 20 determines how fast the natural gas is flowing through the gas upgrading membranes 30. The gas goes through the chiller 20 prior to entering the gas upgrading membranes 30 for desired separation. The flow requires regulation because the efficiency of the gas upgrading membranes 30 depend on the flow rate and the pressure of the incoming natural gas. The efficiency of the membrane depends on the temperature of the incoming gas stream. The flow is regulated to maintain the temperature of the gas and also to remove heavies form the natural gas stream so that heavies don't condense in the In various embodiments, the controller 60 is coupled to the chiller 20 to adjust the operating temperature of the chiller 20. In a preferred embodiment the range for the chiller 20 to operate is between 85 and 100° F. The reduced temperature of operation for the chiller 20 allows the gas to cool down to a lower temperature which in turn increases the efficiency of the gas upgrading membranes 30 leading to better ratio of a desired cut or cuts of natural gas.

In further embodiments, the controller 60 is coupled to a graphical display configured to provide process operating parameters output by the gas chromatographic system 10. Non-limiting examples of process operating parameters include the status of each gas chromatograph, remaining time for an ongoing analysis, and the results of a sample analysis. Additionally, the results of a sample analysis may, for example, be provided as a trace showing each sample constituent as a 'peak' on a horizontal baseline (chromatogram) or as a listing of constituents wherein the peaks of the chromatogram have been identified by a software package. Non-limiting examples of the graphical display include an LCD display, an LED display, a CRT display, and a plasma display. The graphical display may, for example, be a full-color display capable of displaying images, a grayscale display capable of displaying images, a single color display capable of displaying images, or a series of indicator lights/LEDs/beacons.

The graphical display provides information to a human operator. In various embodiments, the information is used for informational or monitoring purposes and the controller 60 automatically adjusts system parameters to optimize the natural gas upgrading operation. In further embodiments, the information provided by the graphical display is used by the human operator to manually adjust system parameters to, for example, optimize the natural gas upgrading operation.

Referring again to FIG. 1, the controller 60 may comprise a processor, and at least one graphical display as an operator interface communicatively coupled to the processor. Various hardware as familiar to one of ordinary skill in the art is contemplated for use in the processor, for example and not by way of limitation, an input/output module, a programmable logic controller, an antenna, power supply, etc. As described below, many of the decision-making and controlling features described in the embodiments below are performed by the programmable logic controller. That being said, alternatives to programmable logic controller are also contemplated, for example, microprocessor controller units. As shown in the embodiment of FIG. 1, the controller 60 may receive data from the at least one upstream gas chromatograph 12 and at least two downstream gas chromatographs 14,16. Based on these data readings, the controller 60 is programmed with instructions to automatically adjust, for example, the inlet flow rate from the natural gas supply feed 70 via the flow regulator 80, the operation of the chiller 20, and/or the operation of the first membrane 40 and the second membrane 50 including flow rates from upgraded product stream outlets 44,46,48 of the first membrane 40 and upgraded product stream outlets 54,56,58 of the second membrane 50.

The information provided by the controller 60 and graphical user interface of the process operating parameters output by the gas chromatographic system 10 allows system parameters to be adjusted to improve or optimize the natural gas upgrading operation both automatically as detailed above or upon input from an operator. For example, if the level of heavy hydrocarbons is too high at the first membrane inlet 42 and the second membrane inlet 52, the temperature in the chiller 20 and/or flow rate of the natural gas supply feed 70 through the chiller 20 may be automatically reduced by the controller 60 to allow additional heavy hydrocarbon removal. Additionally, if the level of nitrogen is too high in the first cut of upgraded natural gas of the first membrane 40 and/or the first cut of upgraded natural gas of the second membrane 50, the first membrane 40 and/or second membrane 50 may be past their useful life and in need of replacement. Alternatively, the first membrane 40 and/or second membrane 50 may have undesirable separation parameters for the natural gas supply feed 70 being processed necessitating replacement with an alternate membrane with more desirable separation parameters. In general, the efficiency of gas upgrading membranes 30 increase when there is a higher difference in the pressure of the incoming natural gas at low temperature. If the nitrogen content is too high, in crude natural gas of the natural gas supply feed 70 the feed pressure of the gas is increased while dropping the temperate by passage through the chiller 20. In the case of low methane, the composition of the membrane material of the gas upgrading membranes 30 is changed.

The complete system can be configured to analyze all components present in the samples of natural gas as one report or it can be divided into two or more sections, so that certain elements of gases are reported in one analytical report and other elements are reported in the second, third, or subsequent analytical report.

The at least two gas upgrading membranes 30 work according to the principle of selective permeation through a membrane surface. The at least two gas upgrading membranes 30 are pressurized with the natural gas mixture exiting the chiller 20. The natural gas components from the natural gas supply feed 70 are separated through the difference in pressure and concentration on the inner and outer sides of the fibers of the at least two gas upgrading membranes 30. During the separation of the components of the natural gas from the natural gas supply feed 70 to form upgraded natural gas streams, carbon dioxide, hydrogen sulfide, C1, C2, C3, C4, C5 and water vapor have a strong preference to permeate through the membrane, whilst the nitrogen is rejected within the membrane for passage out of the membrane as a nitrogen rich stream. In various embodiments, the first membrane 40 and the second membrane 50 are the same or similar in material and construction and are configured to selectively remove substantially the same compositions from the natural gas supply feed 70. In further embodiments, the first membrane 40 and the second membrane 50 are substantially dissimilar in material and/or construction and such that they are configured to selectively remove different compositions from the natural gas supply feed 70 and/or more effectively remove differing compositions from the natural gas supply feed 70. In various embodiments, the material of construction of the first membrane 40 and the second membrane 50 may be any man made polymer such as polydimethylsiloxane (PDMS), poly silicone, polyimide or a combination of such polymers. Most of the gas upgrading membranes 30 are coated with an additional thin layer of secondary polymer solution to make it specific to achieve certain levels of separation based on the application. The polymer sheets are wrapped on a porous steel pipe, making multiple layer of membrane, to achieve the desired separation of gases from each other based on permeability/solubility of each gas.

When selecting the at least two gas upgrading membranes 30 the following factors should be considered: 1. The composition of the natural gas supply feed 70; 2. the desired upgraded natural gas composition; 3. The pressure of the natural gas supply feed 70; and 4. the temperature of the gas prior to entering the at least two gas upgrading membranes 30. These factors are dependent on the kind of membrane and the desired separation to achieved by the at least two gas upgrading membranes 30.

In operation, as shown in FIG. 1, the natural gas upgrading system 100 analyzes the natural gas supply feed 70 both before and after a natural gas upgrading procedure to determine the effectiveness of the at least two gas upgrading membranes 30. Specifically, the natural gas supply feed 70 provides unprocessed natural gas through the chiller 20 to generate a natural gas free of liquids 24. As previously indicated, passage through the chiller 20 removes heavy hydrocarbons as well as liquids from the unprocessed natural gas. The natural gas free of liquids 24 exiting the chiller 20 is then transported to the at least two gas upgrading membranes 30. Passage of the natural gas through the at least two gas upgrading membranes 30 produces at least a first cut of upgraded natural gas, a second cut of upgraded natural gas, and a third cut of upgraded natural gas from both of upgraded product stream outlets 44,46,48 of the first membrane 40 and upgraded product stream outlets 54,56,58 of the second membrane 50.

Further, samples of the natural gas are passed to the gas chromatographic system for analysis. Specifically, a sample of the natural gas exiting the chiller 20, a sample of the natural gas entering the first membrane 40 at the first membrane inlet 42, and a sample of the natural gas entering the second membrane 50 at the second membrane inlet 52 are transported to the at least one upstream gas chromatograph 12. Additionally, a sample of the upgraded natural gas exiting each of the upgraded product stream outlets 44,46, 48,54,56,58 are transported to the at least two downstream gas chromatographs 14,16. In a further embodiment, a sample of the natural gas entering the chiller 20, a sample of the natural gas entering the first membrane 40 at the first membrane inlet 42, and a sample of the natural gas entering the second membrane 50 at the second membrane inlet 52 are transported to the at least one upstream gas chromatograph 12.

Upon receipt of natural gas samples, the at least one upstream gas chromatograph 12 and the at least two downstream gas chromatographs 14,16 simultaneously analyze the composition of the natural gas samples. For example, the at least one upstream gas chromatograph 12 may analyze the composition of the natural gas sample provided from the second membrane inlet 52, the first downstream gas chromatograph 14 may concurrently analyze the composition of the natural gas sample from the product stream outlet 44 placed to provide the first cut of upgraded natural gas of the first membrane 40, and the second downstream gas chromatograph 16 may also concurrently analyze the composition of the natural gas sample from the product stream outlet 58 placed to provide the final cut of upgraded natural gas of the second membrane 50. Other combinations of samples would be known to one skilled in the art based upon the specific disclosure herein of fluid connections between the gas chromatographic system 10 and sample sources such as the at least two gas upgrading membranes 30 and chiller 20.

Examples

For illustration of one or more of the above embodiments, an exemplary system has been provided below. In this exemplary system, the Mole % of various components of the unprocessed natural gas and upgraded natural gas streams is provided. Specifically, eleven different components are monitored by each of the at least one upstream gas chromatograph 12, the first downstream gas chromatograph 14, and the second downstream gas chromatograph 16 to provide a summary of the natural gas upgrading process. The specific data is provided below in Table 1.

| Components | Unprocessed Natural Gas (Mole %) | First Cut, Upgraded Natural Gas (Mole %) | Second Cut, Upgraded Natural Gas (Mole %) | Final Cut, Upgraded Natural Gas (Mole %) |
| --- | --- | --- | --- | --- |
| Nitrogen | 14.3653 | 8.9921 | 11.1276 | 30.7962 |
| Methane | 69.2803 | 70.2751 | 71.7649 | 62.8071 |
| Carbon Dioxide | 3.6051 | 4.3762 | 3.8235 | 1.5822 |
| Ethane | 4.5333 | 5.9664 | 5.0174 | 1.9686 |
| Hydrogen Sulfide | 3.2966 | 4.2830 | 3.3981 | 0.9298 |
| Propane | 1.7053 | 2.3720 | 1.8761 | 0.6252 |
| Isobutane | 0.4027 | 0.5345 | 0.4156 | 0.1386 |
| N-butane | 0.7253 | 0.8648 | 0.7428 | 0.2427 |
| Isopentane | 1.0918 | 1.3120 | 1.0418 | 0.3751 |
| Water | 0.1196 | 0.3159 | 0.2328 | 0.1551 |
| C5+ | 1.0918 | 1.3673 | 1.0837 | 0.3751 |
| SUM | 100.2171 | 100.6593 | 100.5243 | 99.9957 |

It should be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

What is claimed is:

1. A gas chromatographic method for analyzing natural gas, comprising:

transporting the natural gas through a chiller;

transporting the natural gas from the chiller to at least two gas upgrading membranes each comprising at least three upgraded product stream outlets placed to provide a first cut of upgraded natural gas, a second cut of upgraded natural gas, and a third cut of upgraded natural gas respectively;

operating a gas chromatographic system comprising at least one upstream gas chromatograph and at least two downstream gas chromatographs comprising a first downstream gas chromatograph and a second downstream gas chromatograph, wherein the at least one upstream gas chromatograph, the first downstream gas chromatograph, and the second downstream gas chromatograph all operate simultaneously, the at least one upstream gas chromatograph, the first downstream gas chromatograph, and the second downstream gas chromatograph are all calibrated using the same calibration feed, and the at least one upstream gas chromatograph, the first downstream gas chromatograph, and the second downstream gas chromatograph all utilize the same heating oven to heat samples of natural gas;

transporting samples of natural gas to the gas chromatographic system, wherein a sample of the natural gas exiting the chiller, a sample of the natural gas entering a first membrane of the at least two gas upgrading membranes, and a sample of the natural gas entering a second membrane of the at least two gas upgrading membranes are transported to the at least one upstream gas chromatograph, and a sample of the upgraded natural gas exiting each of the upgraded product stream outlets are transported to the at least two downstream gas chromatographs; and monitoring the composition of the sample of the natural gas exiting the chiller, the sample of the natural gas entering a first membrane of the at least two gas upgrading membranes, the sample of the natural gas entering a second membrane of the at least two gas upgrading membranes, and the samples of the upgraded natural gas exiting each of the product stream outlets with a controller to determine upgrading of the natural gas.

2. The method of claim 1, wherein the samples of the upgraded natural gas exiting the product stream outlet placed to provide the first cut of upgraded natural gas is transported to the first downstream gas chromatograph.

3. The method of claim 1, wherein the sample of the upgraded natural gas exiting the product stream outlet placed to provide the second cut of upgraded natural gas from the first membrane is transported to the first downstream gas chromatograph and the sample of the upgraded natural gas exiting the product stream outlet placed to provide the second cut of upgraded natural gas from the second membrane is transported to the second downstream gas chromatograph.

4. The method of claim 1, wherein the samples of the upgraded natural gas exiting the product stream outlet placed to provide the third cut of upgraded natural gas is transported to the second downstream gas chromatograph.

5. A gas chromatographic method for analyzing natural gas, comprising:

transporting the natural gas through a chiller;

transporting the natural gas from the chiller to at least two gas upgrading membranes each comprising at least three upgraded product stream outlets placed to provide a first cut of upgraded natural gas, a second cut of upgraded natural gas, and a third cut of upgraded natural gas respectively;

operating a gas chromatographic system comprising at least one upstream gas chromatograph and at least two downstream gas chromatographs comprising a first downstream gas chromatograph and a second downstream gas chromatograph, wherein the at least one upstream gas chromatograph, the first downstream gas chromatograph, and the second downstream gas chromatograph all operate simultaneously, the at least one upstream gas chromatograph, the first downstream gas chromatograph, and the second downstream gas chromatograph are all calibrated using the same calibration feed, and the at least one upstream gas chromatograph, the first downstream gas chromatograph, and the second downstream gas chromatograph all utilize the same heating oven to heat samples of natural gas;

transporting samples of natural gas to the gas chromatographic system, wherein a sample of the natural gas entering the chiller, a sample of the natural gas entering a first membrane of the at least two gas upgrading membranes, and a sample of the natural gas entering a second membrane of the at least two gas upgrading membranes are transported to the at least one upstream gas chromatograph, and a sample of the upgraded natural gas exiting each of the upgraded product stream outlets are transported to the at least two downstream gas chromatographs; and monitoring the composition of the sample of the natural gas entering the chiller, the sample of the natural gas entering a first membrane of the at least two gas upgrading membranes, the sample of the natural gas entering a second membrane of the at least two gas upgrading membranes, and the samples of the upgraded natural gas exiting each of the product stream outlets with a controller to determine upgrading of the natural gas.

6. The method of claim 5, wherein the samples of the upgraded natural gas exiting the product stream outlet placed to provide the first cut of upgraded natural gas is transported to the first downstream gas chromatograph.

7. The method of claim 5, wherein the sample of the upgraded natural gas exiting the product stream outlet placed to provide the second cut of upgraded natural gas from the first membrane is transported to the first downstream gas chromatograph and the sample of the upgraded natural gas exiting the product stream outlet placed to provide the second cut of upgraded natural gas from the second membrane is transported to the second downstream gas chromatograph.

8. The method of claim 5, wherein the samples of the upgraded natural gas exiting the product stream outlet placed to provide the third cut of upgraded natural gas is transported to the second downstream gas chromatograph.

9. A natural gas upgrading system comprising a gas chromatographic system, a chiller, at least two gas upgrading membranes, and a controller, wherein:
the gas chromatographic system comprises at least one upstream gas chromatograph and at least two downstream gas chromatographs comprising a first downstream gas chromatograph and a second downstream gas chromatograph;
the chiller is configured to remove heavy hydrocarbons from a natural gas supply feed and is fluidly connected to the at least two gas upgrading membranes;
the at least two gas upgrading membranes are configured to selectively allow certain gases to permeate to remove impurities from the natural gas and each comprise an inlet and at least three product stream outlets placed to provide a first cut of upgraded natural gas, a second cut of upgraded natural gas, and a third cut of upgraded natural gas respectively;
the at least one upstream gas chromatograph is fluidly connected to the inlet or exit of the chiller, the inlet of a first membrane of the at least two gas upgrading membranes, and the inlet of a second membrane of the at least two gas upgrading membranes for transport of samples to the at least one upstream gas chromatograph;
each of the product stream outlets is fluidly connected to at least one of the at least two downstream gas chromatographs for transport of samples to the at least two downstream gas chromatographs;

the controller is configured to monitor the composition of the samples of the natural gas from the exit of the chiller, the inlet of the first membrane of the at least two gas upgrading membranes, the inlet of the second membrane of the at least two gas upgrading membranes, and the samples from each of the product stream outlets to determine upgrading of the natural gas; and
the at least one upstream gas chromatograph and the at least two downstream gas chromatographs are configured to operate simultaneously, are calibrated by a single calibration gas feed, and a single heating oven or set of heating ovens in series is provided to heat natural gas samples for the at least one upstream gas chromatograph and the at least two downstream gas chromatographs.

10. The natural gas upgrading system of claim 9, wherein the heavy hydrocarbons are C7 or above.

11. The natural gas upgrading system of claim 9, wherein the product stream outlet placed to provide the first cut of upgraded natural gas of the first membrane and the product stream outlet placed to provide the first cut of upgraded natural gas of the second membrane are fluidly connected to the first downstream gas chromatograph.

12. The natural gas upgrading system of claim 9, wherein the product stream outlet placed to provide the second cut of upgraded natural gas of the first membrane is fluidly connected to the first downstream gas chromatograph and the product stream outlet placed to provide the second cut of upgraded natural gas of the second membrane is fluidly connected to the second downstream gas chromatograph.

13. The natural gas upgrading system of claim 9, wherein the product stream outlet placed to provide the third cut of upgraded natural gas of the first membrane and the product stream outlet placed to provide the third cut of upgraded natural gas of the second membrane are fluidly connected to the second downstream gas chromatograph.

14. The natural gas upgrading system of claim 9, wherein the controller is coupled to a flow regulator configured to controllably adjust the rate at which the natural gas supply feed is provided to the chiller.

15. The natural gas upgrading system of claim 9, wherein the controller is coupled to the chiller to adjust the operating temperature of the chiller.

16. The natural gas upgrading system of claim 9, wherein the controller is coupled to a graphical display configured to provide process operating parameters output by the gas chromatographic system.

17. The natural gas upgrading system of claim 9, wherein the two gas upgrading membranes are configured to selectively remove nitrogen and acid gases from the natural gas supply feed.

* * * * *